(12) United States Patent
Yang et al.

(10) Patent No.: US 9,476,840 B2
(45) Date of Patent: Oct. 25, 2016

(54) METHODS OF INSPECTING A SEMICONDUCTOR DEVICE AND SEMICONDUCTOR INSPECTION SYSTEMS

(71) Applicant: Samsung Electronics Co., Ltd., Suwon-Si, Gyeonggi-Do (KR)

(72) Inventors: Kiho Yang, Hwaseong-si (KR); Seunghune Yang, Seoul (KR); Sibo Cai, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 188 days.

(21) Appl. No.: 14/340,910

(22) Filed: Jul. 25, 2014

(65) Prior Publication Data

US 2015/0110383 A1 Apr. 23, 2015

(30) Foreign Application Priority Data

Oct. 21, 2013 (KR) .................. 10-2013-0125474

(51) Int. Cl.
*G01N 21/956* (2006.01)
*G06K 9/46* (2006.01)
(Continued)

(52) U.S. Cl.
CPC ............ *G01N 21/956* (2013.01); *G01N 21/88* (2013.01); *G01N 21/8851* (2013.01); *G03F 7/70616* (2013.01); *G06K 9/4604* (2013.01); *G06T 7/001* (2013.01); *G06T 7/0006* (2013.01);
(Continued)

(58) Field of Classification Search
CPC . G06T 7/0004; G06T 7/0006; G06T 7/0008; G06T 7/001; G06T 7/0024; G06T 7/0026; G06T 7/60; G06T 2207/20221; G06T 2207/30148; G06T 11/60; G06F 17/5081; H04B 1/16; H01L 27/14605; H01L 27/3276; H01L 29/78606; H01L 29/7869; H01L 51/5284; G01B 11/14; G01B 11/24; G01N 21/956; G01N 21/88; G01N 21/8851; G01N 2021/8854; G01N 2021/8864; G01N 2021/8874; G01N 2021/8887; G01N 2021/95676; G01N 21/9501; G01N 21/9503; G01N 21/9505; G03F 7/70616; G03F 7/7065; G03F 7/70666

See application file for complete search history.

(56) References Cited

U.S. PATENT DOCUMENTS 4,516,261 A * 5/1985 Harding ................ A61B 6/025
  348/E5.086
5,086,477 A * 2/1992 Yu ........................ G06F 17/5068
  348/87

(Continued)

FOREIGN PATENT DOCUMENTS

JP     2010191398 A      9/2010
KR    20060112855 A     11/2006

(Continued)

*Primary Examiner* — Manav Seth
(74) *Attorney, Agent, or Firm* — Harness, Dickey & Pierce, P.L.C.

(57) ABSTRACT

Inventive concepts provide a method of inspecting a semiconductor device including obtaining inspection image data of an inspection pattern of an inspection layer on a substrate. The method may include extracting inspection contour data including an inspection pattern contour from the inspection image data, and merging the inspection contour data with comparison contour data of a comparison layer to obtain merged data. The comparison layer may overlap the inspection layer. The method may also include determining a horizontal distance between the inspection pattern contour and a comparison pattern contour of the comparison contour data based on the merged data.

20 Claims, 5 Drawing Sheets

(51) Int. Cl.
   *G06T 11/60* (2006.01)
   *G01N 21/88* (2006.01)
   *G03F 7/20* (2006.01)
   *G06T 7/00* (2006.01)
(52) U.S. Cl.
   CPC .... *G06T 11/60* (2013.01); *G06T 2207/20221* (2013.01); *G06T 2207/30148* (2013.01)

(56) References Cited

U.S. PATENT DOCUMENTS

| | | | |
|---|---|---|---|
| 5,585,951 A * | 12/1996 | Noda | G02F 1/136227 349/122 |
| 6,228,464 B1 * | 5/2001 | Miyaji | B41M 1/12 428/195.1 |
| 6,479,120 B2 * | 11/2002 | Miyaji | B41M 1/12 156/272.8 |
| 6,586,341 B2 * | 7/2003 | Moniwa | G03F 1/20 430/312 |
| 6,706,456 B2 * | 3/2004 | Miyashita | G03F 7/70058 430/30 |
| 6,970,409 B2 * | 11/2005 | Araki | G11B 7/0045 369/53.24 |
| 7,079,971 B2 * | 7/2006 | Fukuda | G11C 29/56 324/537 |
| 7,268,381 B2 * | 9/2007 | Birner | H01L 27/10864 257/301 |
| 7,326,961 B2 * | 2/2008 | Yamazaki | H01L 21/2022 257/330 |
| 7,403,435 B2 * | 7/2008 | Kato | G11C 11/4074 257/E21.659 |
| 7,545,004 B2 * | 6/2009 | Yang | H01L 21/82380 257/369 |
| 7,667,216 B2 | 2/2010 | Van Den Broeke et al. | |
| 8,037,428 B2 * | 10/2011 | Tong | G03F 1/144 716/51 |
| 8,108,803 B2 | 1/2012 | Heng et al. | |
| 8,111,900 B2 | 2/2012 | Wu et al. | |
| 8,139,843 B2 | 3/2012 | Kulkarni et al. | |
| 8,171,433 B2 * | 5/2012 | Takahashi | G06F 17/5081 430/30 |
| 8,189,903 B2 | 5/2012 | Itoh | |
| 9,244,365 B2 * | 1/2016 | Okamoto | G06T 7/0004 |
| 2002/0110068 A1 * | 8/2002 | Araki | G11B 7/0045 369/53.24 |
| 2002/0175298 A1 * | 11/2002 | Moniwa | G03F 1/20 250/492.22 |
| 2006/0239536 A1 * | 10/2006 | Shibuya | G01N 21/9501 382/149 |
| 2007/0035712 A1 * | 2/2007 | Gassner | G03F 7/70666 355/55 |
| 2007/0052963 A1 * | 3/2007 | Orbon | G03F 7/7065 356/430 |
| 2007/0148562 A1 | 6/2007 | Broeke et al. | |
| 2007/0150850 A1 | 6/2007 | Itoh | |
| 2008/0247632 A1 | 10/2008 | Boehm et al. | |
| 2008/0312400 A1 * | 12/2008 | Yamashita | C08G 77/28 528/30 |
| 2010/0226562 A1 | 9/2010 | Wu et al. | |
| 2011/0099529 A1 | 4/2011 | Heng et al. | |
| 2011/0286656 A1 | 11/2011 | Kulkarni et al. | |
| 2016/0164049 A1 * | 6/2016 | Choi | H01L 51/5253 438/27 |

FOREIGN PATENT DOCUMENTS

| | | |
|---|---|---|
| KR | 100914297 B1 | 8/2009 |
| KR | 20100034611 A | 4/2010 |
| KR | 20100073374 A | 7/2010 |
| KR | 101010754 B1 | 1/2011 |
| KR | 101051687 B1 | 7/2011 |
| KR | 20110088904 A | 8/2011 |
| KR | 101090472 B1 | 12/2011 |

* cited by examiner

METHODS OF INSPECTING A SEMICONDUCTOR DEVICE AND SEMICONDUCTOR INSPECTION SYSTEMS

CROSS-REFERENCE TO RELATED APPLICATION

This U.S. non-provisional patent application claims priority under 35 U.S.C. §119 to Korean Patent Application No. 10-2013-0125474, filed on Oct. 21, 2013, in the Korean Intellectual Property Office, the disclosure of which is hereby incorporated by reference in its entirety.

BACKGROUND

Inventive concepts relate to methods of inspecting a semiconductor device and/or semiconductor inspection systems.

Semiconductor devices are widely used in an electronic industry because of their small size, multi-function and/or low manufacture cost characteristics. Semiconductor devices may be manufactured by various manufacture processes such as a photolithography process, an etching process, a deposition process, an ion implantation process, a cleaning process, and an inspecting process.

In an inspecting process, defects of patterns may be detected in a semiconductor device. However, as semiconductor devices are being highly integrated, patterns are becoming smaller. Thus, it is becoming increasingly difficult to detect defects of semiconductor devices.

SUMMARY

At least one example embodiment of inventive concepts may provide methods of inspecting a semiconductor device capable of improving reliability of inspection.

At least one example embodiment of inventive concepts may also provide semiconductor inspection systems capable of improving reliability of inspection.

At least one example embodiment of inventive concepts may further provide methods of inspecting a semiconductor device capable of precisely detecting defects between real patterns and invisible patterns.

At least one example embodiment of inventive concepts may yet further provide semiconductor inspection systems capable of precisely detecting defects between real patterns and invisible patterns.

According to at least one example embodiment, a method of inspecting a semiconductor device includes obtaining inspection image data of an inspection pattern of an inspection layer on a substrate. The method includes extracting inspection contour data including an inspection pattern contour from the inspection image data. The method includes merging the inspection contour data with comparison contour data of a comparison layer to obtain merged data. The comparison layer may overlap the inspection layer. The method may include determining a horizontal distance between the inspection pattern contour and a comparison pattern contour of the comparison contour data based on the merged data.

According to at least one example embodiment, the comparison layer is not visible during the obtaining operation.

According to at least one example embodiment, the comparison layer is disposed under the inspection layer, a film is on the comparison layer, and the inspection pattern of the inspection layer is on the film.

According to at least one example embodiment, the method further includes obtaining comparison image data of a comparison pattern included in the comparison layer before formation of the inspection layer. The method includes extracting the comparison contour data from the comparison image data.

According to at least one example embodiment, the comparison contour data is from design layout data of the comparison layer.

According to at least one example embodiment, the comparison layer is an upper layer formed on the inspection layer.

According to at least one example embodiment, the comparison contour data is from design layout data of the comparison layer.

According to at least one example embodiment, the method includes comparing the determined horizontal distance with a reference distance.

According to at least one example embodiment, the method includes performing a rework process if the determined horizontal distance is outside a tolerance range of the reference distance.

According to at least one example embodiment, the inspection pattern includes a plurality of inspection patterns, the inspection contour data includes a plurality of inspection pattern contours corresponding to the plurality of inspection patterns, respectively, and the comparison contour data includes a plurality of comparison pattern contours corresponding to the plurality of inspection pattern contours, respectively. The determining a horizontal distance determines a horizontal distance between each of the inspection pattern contours and each of the comparison pattern contours corresponding to the inspection pattern contours. The comparing the determined horizontal distance with the reference distance compares the determined horizontal distances with reference distances corresponding to the determined horizontal distances, respectively.

According to at least one example embodiment, the method includes identifying a hotspot of the inspection patterns by comparing the determined horizontal distances with the reference distances.

According to at least one example embodiment, the inspection contour data is in a geometric database standard (GDS) format.

According to at least one example embodiment, a semiconductor inspection system includes an image detection apparatus configured to obtain inspection image data of an inspection pattern of an inspection layer formed on a substrate; and an electronic system including a controller. The controller is configured to extract inspection contour data including an inspection pattern contour from the inspection image data, merge the inspection contour data with comparison contour data of a comparison layer, and determine a horizontal distance between the inspection pattern contour and a comparison pattern contour of the comparison contour data based on the merged data. The comparison layer overlaps with the inspection layer.

According to at least one example embodiment, the electronic system further includes a memory device configured to store the obtained inspection image data, the extracted inspection contour data, the merged data, the comparison contour data, and the determined horizontal distance.

According to at least one example embodiment, the image detection apparatus is one of a nano geometry research (NGR) apparatus and a scanning electron microscope (SEM) apparatus.

According to at least one example embodiment, a method of inspecting a semiconductor device includes receiving image data of a first pattern on a substrate. The method includes extracting at least one first contour of the first pattern from the image data, and merging the at least one first contour with at least one second contour of a second pattern. The second pattern and the first pattern are at different vertical levels within the semiconductor device. The method includes determining at least one lateral distance between the at least one first contour and the at least one second contour based on the merging.

According to at least one example embodiment, the at least one second contour corresponds to at least one active region in the substrate, and the at least one determined lateral distance is a lateral distance between the at least one first contour and the at least one active region.

According to at least one example embodiment, the at least one second contour corresponds to at least one contact hole of the semiconductor device, and the at least one determined lateral distance is a lateral distance between the at least one first contour and the at least one contact hole.

According to at least one example embodiment, the method includes comparing the at least one determined lateral distance to at least one reference distance, and performing additional processing on the semiconductor device based on the comparing.

According to at least one example embodiment, the method includes extracting the second contour from one of image data of the second pattern and a design layout of the semiconductor device.

BRIEF DESCRIPTION OF THE DRAWINGS

The inventive concepts will become more apparent in view of the attached drawings and accompanying detailed description.

DETAILED DESCRIPTION OF EXAMPLE EMBODIMENTS

Figure 1:
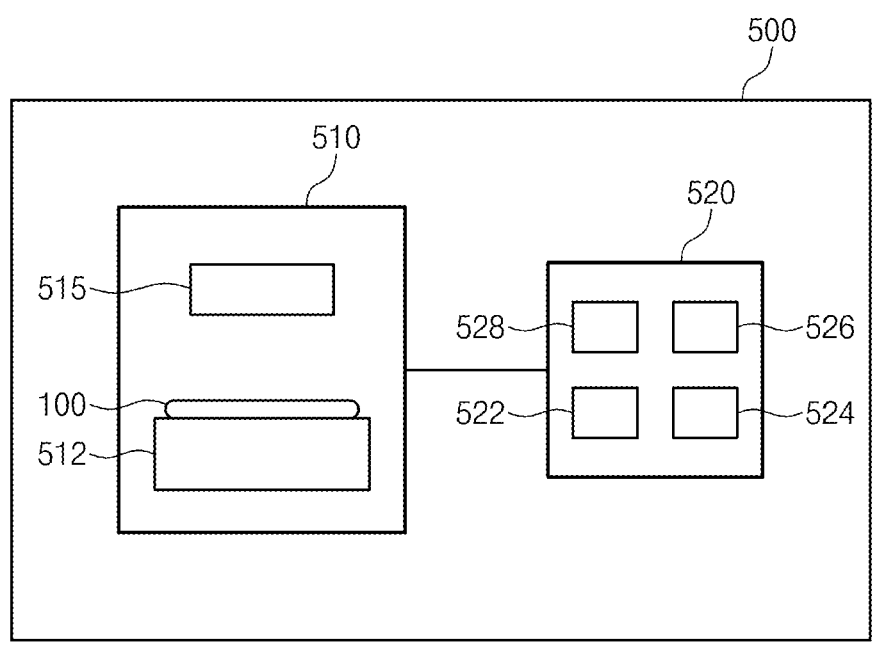
FIG. 1 is a schematic block diagram illustrating a semiconductor inspection system according to at least one example embodiment of inventive concepts.

Inventive concepts will now be described more fully hereinafter with reference to the accompanying drawings, in which exemplary embodiments of inventive concepts are shown. The advantages and features of inventive concepts and methods of achieving them will be apparent from the following exemplary embodiments that will be described in more detail with reference to the accompanying drawings. It should be noted, however, that inventive concepts are not limited to the following exemplary embodiments, and may be implemented in various forms. Accordingly, the exemplary embodiments are provided only to disclose inventive concepts and let those skilled in the art know the category of inventive concepts. In the drawings, example embodiments of inventive concepts are not limited to the specific examples provided herein and are exaggerated for clarity.

The terminology used herein is for the purpose of describing particular embodiments only and is not intended to limit the invention. As used herein, the singular terms "a," "an" and "the" are intended to include the plural forms as well, unless the context clearly indicates otherwise. As used herein, the term "and/or" includes any and all combinations of one or more of the associated listed items. It will be understood that when an element is referred to as being "connected" or "coupled" to another element, it may be directly connected or coupled to the other element or intervening elements may be present.

Similarly, it will be understood that when an element such as a layer, region or substrate is referred to as being "on" another element, it can be directly on the other element or intervening elements may be present. In contrast, the term "directly" means that there are no intervening elements. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Additionally, example embodiments in the detailed description will be described with sectional views as ideal exemplary views of inventive concepts. Accordingly, shapes of the exemplary views may be modified according to manufacturing techniques and/or allowable errors. Therefore, example embodiments of inventive concepts are not limited to the specific shape illustrated in the exemplary views, but may include other shapes that may be created according to manufacturing processes. Areas exemplified in the drawings have general properties, and are used to illustrate specific shapes of elements. Thus, this should not be construed as limited to the scope of inventive concepts.

It will be also understood that although the terms first, second, third etc. may be used herein to describe various elements, these elements should not be limited by these terms. These terms are only used to distinguish one element from another element. Thus, a first element in some example embodiments could be termed a second element in other example embodiments without departing from the teachings of inventive concepts. Exemplary embodiments of aspects of inventive concepts explained and illustrated herein include their complementary counterparts. The same reference numerals or the same reference designators denote the same elements throughout the specification.

Moreover, exemplary embodiments are described herein with reference to cross-sectional illustrations and/or plane illustrations that are idealized exemplary illustrations. Accordingly, variations from the shapes of the illustrations as a result, for example, of manufacturing techniques and/or tolerances, are to be expected. Thus, exemplary embodiments should not be construed as limited to the shapes of regions illustrated herein but are to include deviations in shapes that result, for example, from manufacturing. For example, an etching region illustrated as a rectangle will, typically, have rounded or curved features. Thus, the regions illustrated in the figures are schematic in nature and their shapes are not intended to illustrate the actual shape of a region of a device and are not intended to limit the scope of example embodiments.

Although corresponding plan views and/or perspective views of some cross-sectional view(s) may not be shown, the cross-sectional view(s) of device structures illustrated herein provide support for a plurality of device structures that extend along two different directions as would be illustrated in a plan view, and/or in three different directions as would be illustrated in a perspective view. The two different directions may or may not be orthogonal to each other. The three different directions may include a third direction that may be orthogonal to the two different directions. The plurality of device structures may be integrated in a same electronic device. For example, when a device structure (e.g., a memory cell structure or a transistor structure) is illustrated in a cross-sectional view, an electronic device may include a plurality of the device structures (e.g., memory cell structures or transistor structures), as would be illustrated by a plan view of the electronic device. The plurality of device structures may be arranged in an array and/or in a two-dimensional pattern.

In the following description, illustrative example embodiments will be described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware in existing electronic systems (e.g., electronic imaging systems, image processing systems, digital point-and-shoot cameras, personal digital assistants (PDAs), smartphones, tablet personal computers (PCs), laptop computers, etc.). Such existing hardware may include one or more Central Processing Units (CPUs), digital signal processors (DSPs), application-specific-integrated-circuits (ASICs), field programmable gate arrays (FPGAs) computers or the like.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "memory", "storage medium", "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible or non-transitory machine readable mediums for storing information. The term "computer-readable medium" may include, but is not limited to, portable or fixed storage devices, optical storage devices, and various other tangible or non-transitory mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

FIG. 1 is a schematic block diagram illustrating a semiconductor inspection system according to at least one example embodiment of inventive concepts.

Referring to FIG. 1, a semiconductor inspection system 500 according to example embodiments may include an image detection apparatus 510 and an electronic system 520. The image detection apparatus 510 may include a chuck 512 and an image capture unit 515. A semiconductor substrate 100 may be loaded on the chuck 512. The image capture unit 515 may obtain an image of a pattern formed on the semiconductor substrate 100. The image capture unit 515 may obtain the image using a source such as an electron beam. In at least one example embodiment, the image detection apparatus 510 may be a nano geometry research (NGR) apparatus, which is a geometry verification apparatus. In at least one other example embodiment, the image detection apparatus 510 may be a scanning electron microscope (SEM) apparatus.

The electronic system 520 may receive and process image data obtained from the image detection apparatus 510. The electronic system 520 may include a controller 522 capable of receiving and processing various data, and a memory device 524 capable of storing various data. Functions of the controller 522 and the memory device 524 will be described in more detail later. Additionally, the electronic system 520 may further include an input/output (I/O) unit 526 and an interface unit 528. The I/O unit 526 may include a keyboard, a keypad, and/or a display device. The data obtained from the image inspection apparatus 510 may be transmitted to the electronic system 520 through the interface unit 528. Additionally, data processed in the electronic system 520 may be transmitted to the image inspection apparatus 510 through the interface unit 528. The interface unit 528 may include a cable element, a wireless element, and/or a universal serial bus (USB) port. The controller 522, the memory device 524, the I/O unit 526 and the interface unit 528 may be combined with each other via a data bus. The electronic system 520 may be a computing system.

A method of inspecting a semiconductor device may be performed using the semiconductor inspection system 500 described above. Hereinafter, the inspecting method will be described.

Figure 2:
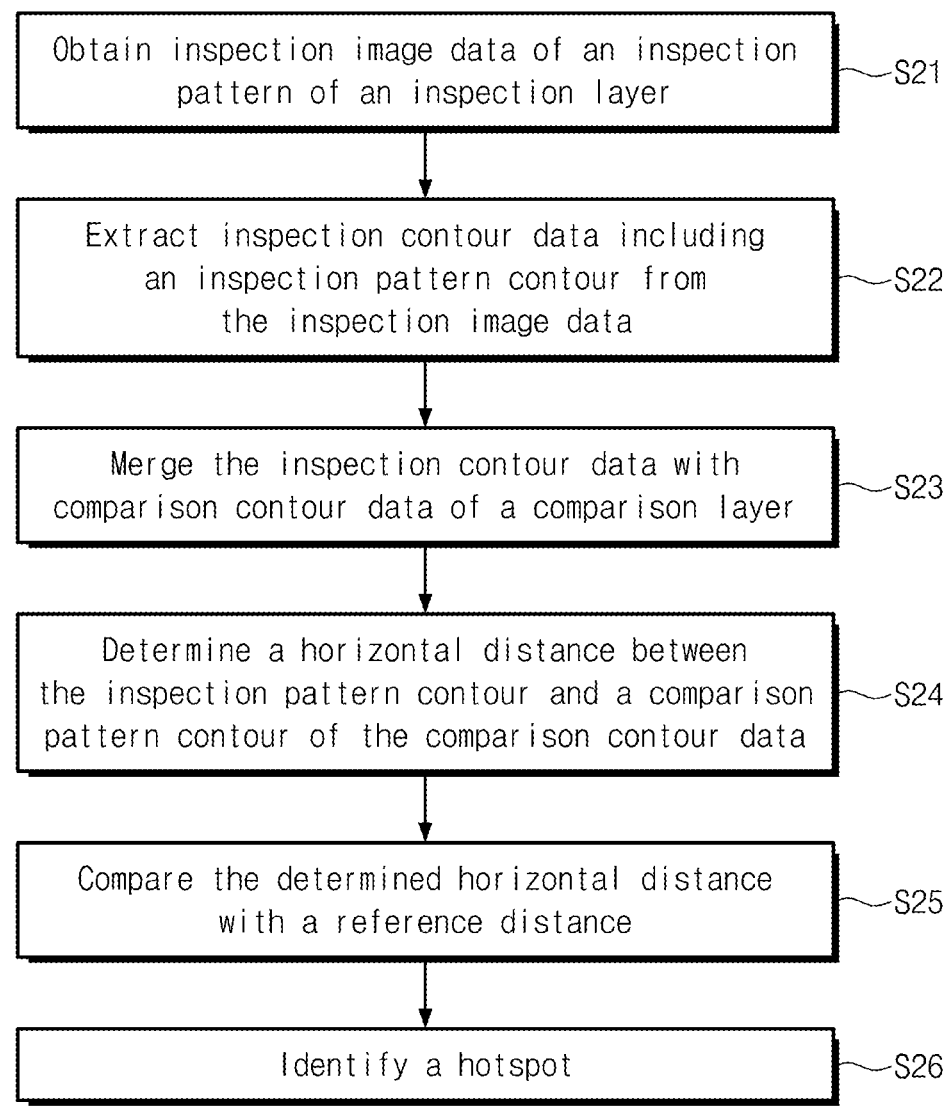
FIG. 2 is a flowchart illustrating a method of inspecting a semiconductor device according to at least one example embodiment of inventive concepts.
Figure 3:
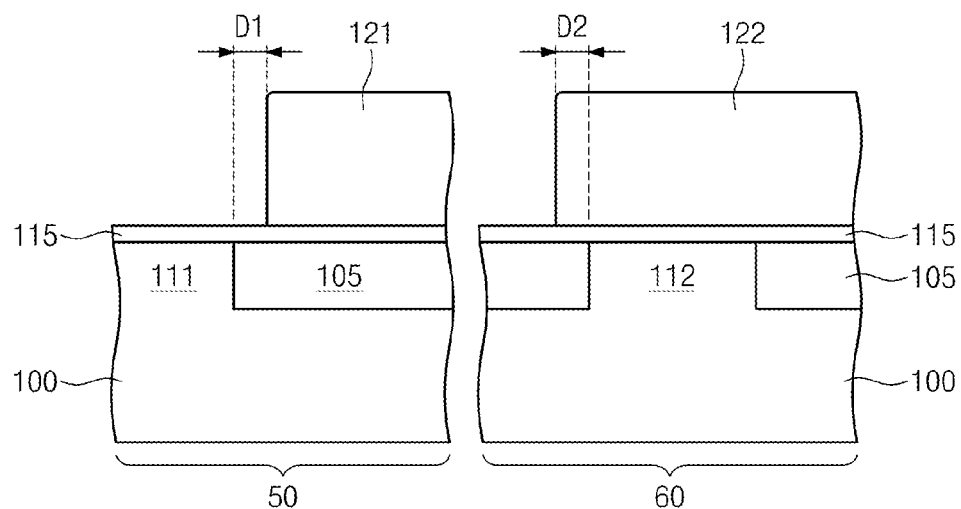
FIG. 3 is a cross-sectional view illustrating a method of inspecting a semiconductor device according to at least one example embodiment of inventive concepts.
Figure 4:
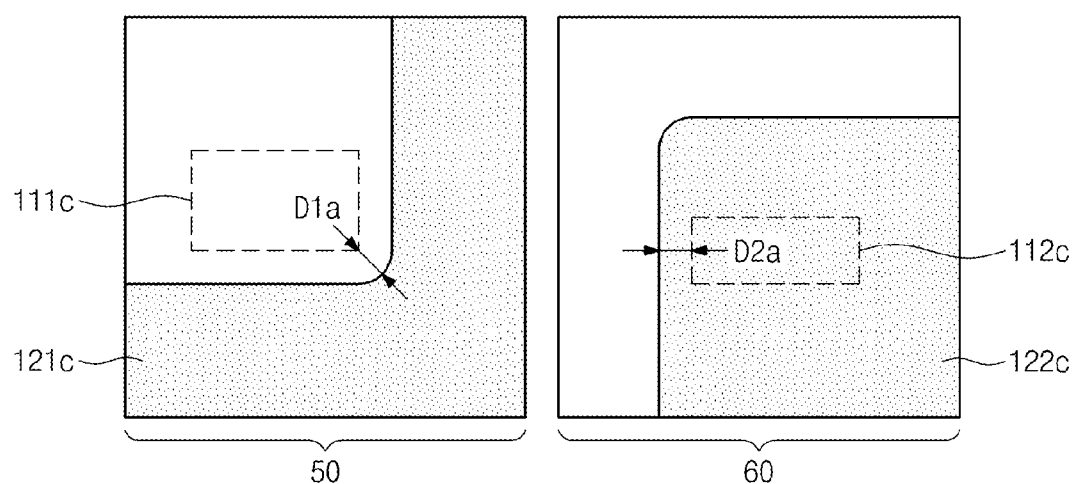
FIG. 4 is a plan view illustrating merged data used in a method of inspecting a semiconductor device according to at least one example embodiment of inventive concepts.

FIG. 2 is a flowchart illustrating a method of inspecting a semiconductor device according to at least one example embodiment of inventive concepts. FIG. 3 is a cross-sectional view illustrating a method of inspecting a semiconductor device according to at least one example embodiment of inventive concepts. FIG. 4 is a plan view illustrating merged data used in a method of inspecting a semiconductor device according to at least one example embodiment of inventive concepts.

As illustrated in FIG. 3, a semiconductor substrate 100 may include a first region 50 and a second region 60. A device isolation pattern 105 may be formed in the semiconductor substrate 100 to define one or more active regions 111 and 112. In at least one example embodiment, a first active region 111 may be defined in the first region 50 and a second active region 112 may be defined in the second region 60.

A material film 115 may be formed on the semiconductor substrate 100. In at least one example embodiment, the material film 115 may perform an ion implantation buffer function, an anti-reflection function, and/or an image supplementary function. The ion implantation buffer function may be a function of protecting the active regions 111 and 112 during a subsequent ion implantation process. The anti-reflection function may be a function of reducing (or alternatively, preventing) reflection of light in a subsequent photolithography process. The image supplementary function may improve an image when the image is obtained from a pattern formed on the material film 115 by using the electron beam. In at least one example embodiment, the material film 115 may include at least one of a silicon oxide film, a silicon oxynitride film, a silicon nitride film, and a carbon film. For example, the carbon film may perform the image supplementary function.

Referring to FIG. 3, an inspection layer including one or more inspection patterns 121 and 122 may be formed on the material film 115. In at least one example embodiment, a first inspection pattern 121 may be formed on the material film 115 in the first region 50 and a second inspection pattern 122 may be formed on the material film 115 in the second region 60. In at least one example embodiment, the first and second inspection patterns 121 and 122 may be photoresist patterns. In other words, a photolithography process may be performed to form the first and second inspection patterns 121 and 122 on the material film 115. The inspection patterns 121 and 122 are real patterns disposed in a chip region of the semiconductor substrate 100. In other words, the inspection patterns 121 and 122 are not disposed in a scribe lane of the semiconductor substrate 100.

In at least one example embodiment, the inspection layer may be a well ion implantation mask layer. The well ion implantation mask layer may expose a region in which a well region will be formed but may cover a region in which the well region will not be formed. In at least one example embodiment, a first well region may be formed in the first active region 111 and a second well region may be formed in the second active region 112. The well ion implantation mask layer may be a mask layer for the formation of the first well region. Thus, the first inspection pattern 121 may not cover the first active region 111 but the second inspection pattern 122 may cover the second active region 112.

Referring to FIGS. 1, 2 and 3, the inspection system 500 obtains inspection image data of the one or more inspection patterns 121 and 122 of the inspection layer in operation (S21). For example, the inspection image data may be obtained by the image detection apparatus 510 of the semiconductor inspection system 500. In more detail, the semiconductor substrate 100 including the inspection patterns 121 and 122 may be loaded on the chuck 512 of the image detection apparatus 510 and the inspection image data may be then obtained using the image capture unit 515. The inspection image data may include image patterns that correspond to the inspection patterns 121 and 122, respectively.

The inspection image data may be stored in the memory device 524 of the electronic system 520. Additionally, the memory device 524 may further store commands for controlling the controller 522. The memory device 524 may include a non-volatile computer readable medium. For example, the memory device 524 may include a hard disk and/or a non-volatile memory device (e.g., a flash memory device, a phase change memory device, and/or a magnetic memory device). The inspection image data may be stored in the memory device 524 through the interface unit 528 of the electronic system 520.

Referring to FIGS. 1 to 4, the inspection system 500 may extract inspection contour data including one or more inspection pattern contours 121c and 122c from the inspection image data in operation (S22). As illustrated in FIG. 4, the inspection contour data includes the inspection pattern contours 121c and 122c respectively corresponding to the image patterns of the inspection image data. The image patterns of the inspection image data may include profile information of the inspection patterns 121 and 122. The inspection pattern contours 121c and 122c may be extracted using the profile information of the inspection patterns 121 and 122 included in the inspection image data. The inspection pattern contours 121c and 122c may correspond to contours of regions of the inspection patterns 121 and 122 capable of performing a desired function (e.g., a mask function) of the inspection patterns 121 and 122. For example, if a sidewall of each of the inspection patterns 121 and 122 is a downward slope, a thickness of each of the inspections patterns 121 and 122 may become reduced from a center to an edge of each of the inspection patterns 121 and 122. In this case, the inspection pattern contours 121c and 122c may correspond to outlines having a minimum thickness capable of achieving the desired function of the inspection patterns 121 and 122.

The controller 522 of the electronic system 520 may extract the inspection contour data from the inspection image data in operation (S22). The extracted inspection contour data may be stored in the memory device 524 of the electronic system 520. In at least one example embodiment, the inspection contour data may be a geometry database standard (GDS) format.

The electronic system 520 may merge inspection contour data with comparison contour data of a comparison layer in operation (S23). The comparison layer vertically overlaps with the inspection layer. In at least one example embodiment, the comparison layer may be disposed under the inspection layer. The comparison layer may include comparison patterns respectively corresponding to the inspection patterns 121 and 122. For example, the comparison patterns of the comparison layer may be the first and second active regions 111 and 112. In other words, the first and second active regions 111 and 112 may be first and second comparison patterns, respectively. The comparison patterns are also disposed in the chip region like the inspection patterns 121 and 122. In other words, the comparison patterns are not disposed in the scribe lane.

The first and second active regions 111 and 112 may correspond to the first and second inspection patterns 121 and 122, respectively. In at least one example embodiment, the first inspection pattern 121 may be laterally spaced apart from the first active region 111 corresponding to the first comparison pattern when viewed from a plan view. The second inspection pattern 122 may vertically overlap with the second active region 112 corresponding to the second comparison pattern.

When the inspection image data of the inspection layer is obtained, the comparison layer is not visible. In other words, the comparison layer is not shown in the inspection image data. In at least one example embodiment, since the material film 115 covers the comparison layer including the first and second active regions 111 and 112, the comparison layer may be hidden.

The comparison contour data may include comparison pattern contours 111c and 112c respectively corresponding to the comparison patterns. The comparison contour data may be stored in the memory device 524 of the electronic system 520. In at least one example embodiment, the comparison contour data may be the GDS format.

The controller 522 may merge the inspection contour data with the comparison contour data to obtain merged data in operation (S23). FIG. 4 illustrates the merged data. The merged data may be stored in the memory device 524 of the electronic system 520. In at least one example embodiment, the merged data may also be the GDS format.

In at least one example embodiment, the comparison contour data may be based on a design layout data of the comparison layer. In other words, the comparison pattern contours 111c and 112c may be pattern contours of the design layout of the first and second active regions 111 and 112.

Figure 5:
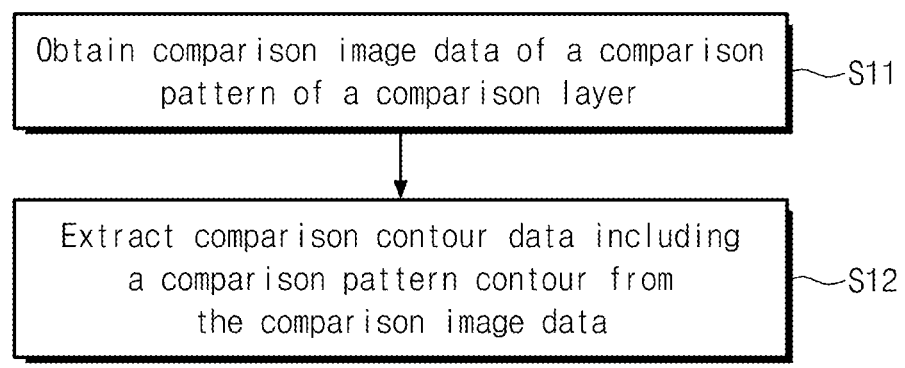
FIG. 5 is a flowchart illustrating an example of a method of obtaining comparison contour data in a method of inspecting a semiconductor device according to at least one example embodiment of inventive concepts.

In at least one example embodiment, the comparison contour data under the inspection layer may be obtained by a similar method to the method of obtaining the inspection contour data. This will be described with reference to FIG. 5 in more detail. FIG. 5 is a flowchart illustrating an example of a method of obtaining comparison contour data in a method of inspecting a semiconductor device according to at least one example embodiment of inventive concepts.

Referring to FIGS. 1, 3, 4 and 5, the inspection system 500 may obtain comparison image data of the comparison patterns of the comparison layer in operation (S11). For example, the comparison image data of the comparison layer including the active regions 111 and 112 may be obtained before the formation of the material film 115. In more detail, the semiconductor substrate 100 having the active regions 111 and 112 may be loaded on the chuck 512 of the image detection apparatus 510 before the material film 115 is formed. The image capture unit 515 may obtain the comparison image data of the active regions 111 and 112. The obtained comparison image data may be stored in the memory device 524 through the interface unit 528.

The controller 522 may extract the comparison contour data including comparison pattern contours 111c and 112c from the comparison image data in operation (S12). In at least one example embodiment, the extracted comparison contour data may be the GDS format. The extracted comparison contour data may be stored in the memory device 524.

Referring again to FIGS. 1 to 4, the controller 522 may determine horizontal distances D1a and D2a between the inspection pattern contours 121c and 122c and the comparison pattern contours 111c and 112c from the merged data in operation (S24). The controller 522 may determine a first horizontal distance D1a between the first inspection pattern contour 121c and the first comparison pattern contour 111c corresponding thereto. The controller 522 may determine a second horizontal distance D2a between the second inspection pattern contour 122c and the second comparison pattern contour 112c corresponding thereto.

The first horizontal distance D1a may correspond to a horizontal distance D1 between the first inspection pattern 121 and the first active region 111 laterally spaced apart from the first inspection pattern 121 in FIG. 3. That is, the first horizontal distance D1a may show a separation degree between the first inspection pattern 121 and the first active region 111 (i.e., the first comparison pattern. The second horizontal distance D2a may correspond to a horizontal distance D2 between a sidewall of the second inspection pattern 122 and a sidewall of the second active region 112 covered by the second inspection pattern 122. That is, the second horizontal distance D2a may show a degree of overlap between the second inspection pattern 122 and the second active region 112 (i.e., the second comparison pattern).

The controller 522 may compare the determined distances D1a and D2a with reference distances in operation (S25). The reference distances include first and second reference distances corresponding to the determined first and second horizontal distances D1a and D2a, respectively. The reference distances are distances for driving of a semiconductor device. The reference distances may be designed distances. In at least one example embodiment, each reference distance may have a tolerance range. For example, the tolerance range of each reference distance may be a range from each reference distance minus a tolerance to each reference distance plus the tolerance (e.g., each reference distance–the tolerance≤the tolerance range of each reference distance≤each reference distance+the tolerance). Comparing the determined horizontal distances D1a and D2a with the reference distances may include confirming whether the determined horizontal distances D1a and D2a are included in the tolerance ranges of the reference distances or not.

The controller 522 may store comparison result data obtained in the comparison operation S25 in the memory device 524.

The controller 522 may identify a hotspot based on the comparison result data in operation (S26). The hotspot may be a region having a possibility of causing a defect on the semiconductor substrate 100. In the hotspot, the determined horizontal distance may exist in an edge of the tolerance range of the reference distance corresponding thereto or may be beyond the tolerance range.

The identified region corresponding to the hotspot may be continuously monitored afterward. If the determined horizontal distance is beyond the tolerance range, a rework process may be performed on the inspection layer including the inspection patterns 121 and 122. In other words, the inspection patterns 121 and 122 of the photoresist patterns may be removed by an ashing process and a recipe of the photolithography process may be then readjusted. A photolithography process may be performed with the readjusted recipe to re-form inspection patterns.

In at least one example embodiment, a design layout of the inspection layer and/or a design layout of the comparison layer may be modified using the comparison result data and/or the identified hotspot. In at least one other example embodiments, both the readjustment of the photolithography process and the modification of the design layout may be performed using the comparison result data and/or the identified hotspot.

The result data of the hotspot may be stored in the memory device 524.

In at least one example embodiment, the inspection image data may be obtained by scanning an entire portion of the chip region. For example, the entire portion of the chip region may be scanned by the NGR apparatus. In this case, the comparison contour data corresponding to the entire portion of the chip region may be merged with the inspection image data. In this case, hotspots that are not verified by a verification simulation may be identified.

According to the aforementioned example embodiments of inventive concepts, it is possible to accurately verify a relative location between the inspection layer and the comparison layer that is not visible when the inspection image data is obtained. Thus, the hotspot of the semiconductor device may be easily and accurately verified. As a result, the semiconductor device having excellent characteristics may be realized and productivity of the semiconductor device may be improved.

In example embodiments described above, the inspection layer may be the ion implantation mask layer. However, inventive concepts are not limited thereto. In at least one example embodiment, the inspection layer may be an etch mask layer.

In the aforementioned example embodiments, the inspection patterns of the inspection layer may be the photoresist patterns. However, inventive concepts are not limited thereto. In at least one example embodiment, the inspection patterns may be real semiconductor patterns such as gate patterns, interconnection patterns, contact patterns and/or pad patterns. In this case, the comparison layer under the inspection layer may be another kind of a layer corresponding to the inspection patterns.

The inspecting method described above may be applied to other layers. For example, the inspection layer may include photoresist patterns defining gate patterns and the comparison layer may include active regions. In at least one example embodiment, the inspection layer may include photoresist patterns defining interconnection patterns and the comparison layer may include contact patterns covered by the interconnection patterns. In at least one other example embodiment, the inspection layer may include photoresist patterns defining landing pad patterns and the comparison layer may include contact patterns covered by the landing pad patterns. However, inventive concepts are not limited thereto. That is, the inspection layer may be one of layers constituting a semiconductor device and the comparison layer may be formed under the inspection layer.

In the aforementioned example embodiments, the comparison layer is disposed under the inspection layer. However, inventive concepts are not limited thereto. In at least one other example embodiment, the comparison layer may be an upper layer that will be formed on the inspection layer. This will be described with reference to FIGS. 6 and 7.

Figure 6:
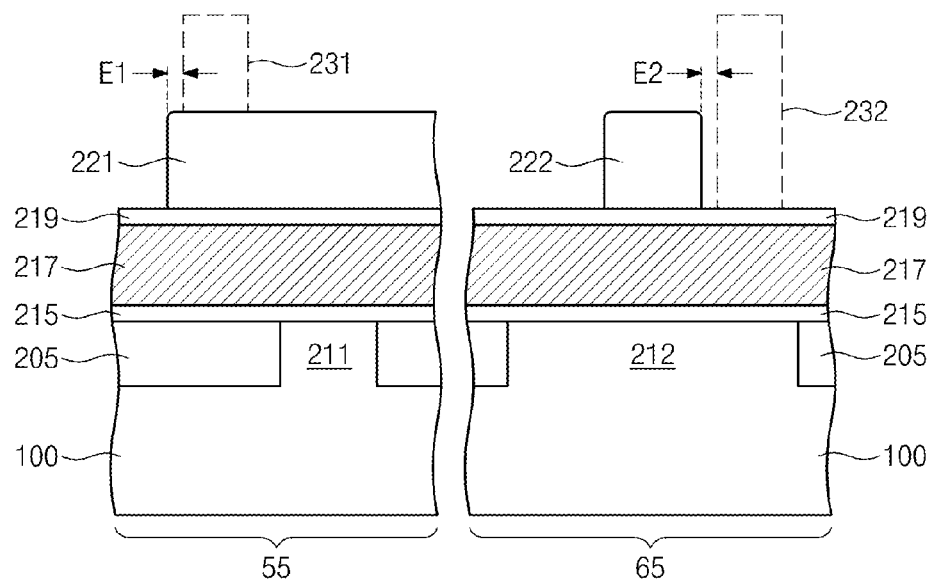
FIG. 6 is a cross-sectional view illustrating a method of inspecting a semiconductor device according to at least one example embodiment of inventive concepts.
Figure 7:
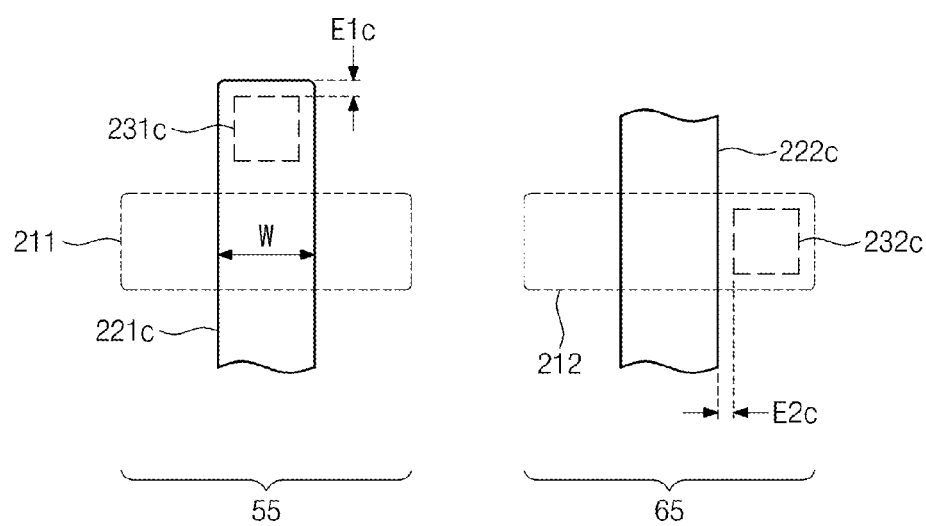
FIG. 7 is a plan view illustrating merged data used in a method of inspecting a semiconductor device according to at least one example embodiment of inventive concepts.

FIG. 6 is a cross-sectional view illustrating a method of inspecting a semiconductor device according to at least one example embodiment of inventive concepts. FIG. 7 is a plan view illustrating a merged data used in a method of inspecting a semiconductor device according to at least one example embodiment of inventive concepts.

Referring to FIG. 6, a device isolation pattern 205 may be formed in or on a semiconductor substrate 100 to define active regions 211 and 212. A first active region 211 and a second active region 212 may be defined in a first region 55 and a second region 65 of the semiconductor substrate 100, respectively. The first and second regions 55 and 65 are included in a chip region of the semiconductor substrate 100.

A gate insulating layer 215, a gate conductive layer 217 and a capping insulating layer 219 may be sequentially formed on the semiconductor substrate 100. The gate insulating layer 215 may include a silicon oxide layer and/or a high-k dielectric layer. The gate conductive layer 217 may include at least one of a doped semiconductor layer (e.g., a doped silicon layer), a metal layer (e.g., a tungsten layer, a titanium layer, and/or a tantalum layer), a conductive metal nitride layer (e.g., a titanium nitride layer, a tantalum nitride layer, and/or a tungsten nitride layer), and a semiconductor-metal compound layer (e.g., a metal silicide layer). The capping insulating layer 219 may include a silicon oxide layer, a silicon nitride layer, and/or a silicon oxynitride layer.

An inspection layer including inspection patterns 221 and 222 may be formed on the capping insulating layer 219. In at least one example embodiment, a first inspection pattern 221 and a second inspection pattern 222 may be formed in the first region 55 and the second region 65, respectively. In at least one example embodiment, the first and second inspection patterns 221 and 222 may be photoresist patterns defining gate patterns. The first and second inspection patterns 221 and 222 may cross over the first and second active regions 211 and 212, respectively. The first and second inspection patterns 221 and 222 are disposed in the chip region.

Referring to FIGS. 1, 2 and 6, the image detection apparatus 510 may obtain inspection image data of the inspection patterns 221 and 222 of the inspection layer in operation (S21). In more detail, the semiconductor substrate 100 having the inspection patterns 221 and 222 may be loaded on the chuck 512 and then the image capture unit 515 may obtain the inspection image data.

Referring to FIGS. 1, 2, 6 and 7, the controller 522 may extract inspection contour data including inspection pattern contours 221c and 222c from the inspection image data of the inspection patterns 221 and 222 in operation (S22). The extracted inspection contour data may be stored in the memory device 524. First and second inspection pattern contours 221c and 222c of the inspection contour data may correspond to contours of the first and second inspection patterns 221 and 222, respectively. The inspection contour data may be in a GDS format.

The controller 522 may merge the inspection contour data with a comparison contour data of a comparison layer in operation (S23). The comparison layer may be the upper layer that will be formed on the inspection layer. In at least one example embodiment, the comparison layer may include first and second comparison patterns 231 and 232 respectively corresponding to the first and second inspection patterns 221 and 222. The first and second comparison patterns 231 and 232 may be formed in the chip region. In at least one example embodiment, the first comparison pattern 231 may be a first contact hole that will expose a first gate pattern defined by the first inspection pattern 221, and the second comparison pattern 232 may be a second contact hole that will expose the second active region 212 at a side of a second gate pattern defined by the second inspection pattern 222.

The comparison contour data may include first and second comparison pattern contours 231c and 232c corresponding to the first and second patterns 231 and 232, respectively. In at least one example embodiment, the comparison contour data may be based on design layout data. In other words, the first and second comparison pattern contours 231c and 232c may be pattern contours of a design layout. The comparison contour data may be in a GDS format.

The comparison contour data may be stored in the memory device 524 before the inspection contour data is merged with the comparison contour data. The merged data may be stored in the memory device 524. FIG. 7 illustrates the merged data. The active regions 211 and 212 are illustrated in FIG. 7. In at least one example embodiment, the merged data may further include contour data of the active regions 211 and 212. Alternatively, the merged data may not include the contour data of the active regions 211 and 212.

Referring to FIGS. 1, 2, 6 and 7, the controller 522 may determine horizontal distances E1c and E2c between the inspection pattern contours 221c and 222c and the comparison pattern contours 231c and 232c from the merged data in operation (S24). In more detail, the controller 522 may determine a first horizontal distance E1c between the first inspection pattern contour 221c and the first comparison pattern contour 231c. The controller 522 may determine a second horizontal distance E2c between the second inspection pattern contour 222c and the second comparison pattern contour 232c. The first horizontal distance E1c may correspond to a horizontal distance E1 between a sidewall of the first inspection pattern 221 and a sidewall of the first comparison pattern 231 that will be formed on the first inspection pattern 221. The second horizontal distance E2c may correspond to a horizontal distance E2 between the second inspection pattern 222 and the second comparison pattern 232 that will be formed at a side of the second inspection pattern 222.

The determined horizontal distances E1c and E2c may be stored in the memory device 524.

The controller 522 compares the determined distances E1c and E2c with reference distances in operation (S25). The reference distances include first and second reference distances corresponding to the checked first and second horizontal distances E1c and E2c, respectively. Each of the reference distances may have a tolerance range. Comparing the determined horizontal distances E1c and E2c with the reference distances may include confirming whether the determined horizontal distances E1c and E2c are respectively included in the tolerance ranges of the reference distances or not.

Comparison result data obtained in the comparing operation S25 may be stored in the memory device 524.

The controller 522 may identify a hotspot based on the comparison result data in operation (S26). Hotspot result data may be stored in the memory device 524. A rework process through a recipe readjustment of a photolithography process and/or modification of the design layout may be performed using the comparison result data and/or the hotspot result data.

According to the inspecting method described above, it is possible to confirm relative locations between the inspection patterns 221 and 222 and the comparison patterns that will be formed. Thus, defects that may occur in a subsequent process may be reduced (or alternatively, prevented). As a result, semiconductor devices having excellent characteristics and/or reliability may be realized and productivity of the semiconductor device may be improved.

In the inspecting method described above, the inspection layer and the comparison layer may be other layers. For example, the inspection layer may include contact patterns. The comparison layer may include interconnections or landing pad patterns that will be formed on the contact patterns. In at least one example embodiment, the inspection layer may include active regions, and the comparison layer may include gate patterns that will be formed on the active regions. However, inventive concepts are not limited to aforementioned example embodiments. In other words, the inspection layer may be one of layers constituting the semiconductor device, and the comparison layer may be an upper layer that will be formed on the inspection layer.

The relative location relation between the inspection layer and the comparison layer may be accurately verified in aforementioned example embodiments of inventive concepts. Thus, the semiconductor device having excellent characteristics and/or reliability may be realized and the productivity of the semiconductor device may be improved.

While inventive concepts have been described with reference to example embodiments, it will be apparent to those skilled in the art that various changes and modifications may be made without departing from the spirits and scopes of inventive concepts. Therefore, it should be understood that the above example embodiments are not limiting, but illustrative. Thus, scopes of inventive concepts are to be determined by the broadest permissible interpretation of the following claims and their equivalents, and shall not be restricted or limited by the foregoing description.

What is claimed is:

1. A method of inspecting a semiconductor device, the method comprising:
   obtaining inspection image data of an inspection pattern of an inspection layer on a substrate;
   extracting inspection contour data including an inspection pattern contour from the inspection image data by an electronic system;
   merging the inspection contour data with comparison contour data of a comparison layer to obtain merged data, the comparison layer overlapping the inspection layer; and
   determining a horizontal distance between the inspection pattern contour and a comparison pattern contour of the comparison contour data based on the merged data.

2. The method of claim 1, wherein the comparison layer is not visible during the obtaining operation.

3. The method of claim 1, wherein the comparison layer is disposed under the inspection layer,
   wherein a film is on the comparison layer, and
   wherein the inspection pattern of the inspection layer is on the film.

4. The method of claim 3, further comprising:
   obtaining comparison image data of a comparison pattern included in the comparison layer before formation of the inspection layer; and
   extracting the comparison contour data from the comparison image data.

5. The method of claim 3, wherein the comparison contour data is from design layout data of the comparison layer.

6. The method of claim 1, wherein the comparison layer is an upper layer formed on the inspection layer.

7. The method of claim 6, wherein the comparison contour data is from design layout data of the comparison layer.

8. The method of claim 1, further comprising:
   comparing the determined horizontal distance with a reference distance.

9. The method of claim 8, further comprising:
   performing a rework process if the determined horizontal distance is outside a tolerance range of the reference distance, wherein the inspection pattern is a photoresist pattern.

10. The method of claim 8, wherein the inspection pattern includes a plurality of inspection patterns,
    wherein the inspection contour data includes a plurality of inspection pattern contours corresponding to the plurality of inspection patterns, respectively,
    wherein the comparison contour data includes a plurality of comparison pattern contours corresponding to the plurality of inspection pattern contours, respectively,
    wherein the determining a horizontal distance determines a horizontal distance between each of the inspection pattern contours and each of the comparison pattern contours corresponding to the inspection pattern contours, and wherein the comparing the determined horizontal distance with the reference distance compares the determined horizontal distances with reference distances corresponding to the determined horizontal distances, respectively.

11. The method of claim 10, further comprising:
identifying a hotspot of the inspection patterns by comparing the determined horizontal distances with the reference distances.

12. The method of claim 1, wherein the inspection contour data is in a geometric database standard (GDS) format.

13. A semiconductor inspection system comprising:
an image detection apparatus configured to obtain inspection image data of an inspection pattern of an inspection layer formed on a substrate; and
an electronic system including a controller, the controller being configured to,
   extract inspection contour data including an inspection pattern contour from the inspection image data,
   merge the inspection contour data with comparison contour data of a comparison layer, and
   determine a horizontal distance between the inspection pattern contour and a comparison pattern contour of the comparison contour data based on the merged data,
wherein the comparison layer overlaps with the inspection layer.

14. The semiconductor inspection system of claim 13, wherein the electronic system further comprises:
a memory device configured to store the obtained inspection image data, the extracted inspection contour data, the merged data, the comparison contour data, and the determined horizontal distance.

15. The semiconductor inspection system of claim 13, wherein the image detection apparatus is one of a nano geometry research (NGR) apparatus and a scanning electron microscope (SEM) apparatus.

16. A method of inspecting a semiconductor device, the method comprising:
receiving image data of a first pattern on a substrate;
extracting at least one first contour of the first pattern from the image data;
merging the at least one first contour with at least one second contour of a second pattern, the second pattern and the first pattern being at different vertical levels within the semiconductor device; and
determining at least one lateral distance between the at least one first contour and the at least one second contour based on the merging.

17. The method of claim 16, wherein the at least one second contour corresponds to at least one active region in the substrate, and the at least one determined lateral distance is a lateral distance between the at least one first contour and the at least one active region.

18. The method of claim 16, wherein the at least one second contour corresponds to at least one contact hole of the semiconductor device, and the at least one determined lateral distance is a lateral distance between the at least one first contour and the at least one contact hole.

19. The method of claim 16, further comprising:
comparing the at least one determined lateral distance to at least one reference distance; and
performing additional processing on the semiconductor device based on the comparing.

20. The method of claim 16, further comprising:
extracting the second contour from one of image data of the second pattern and a design layout of the semiconductor device.

* * * * *